United States Patent
Kelner (10) Patent No.: US 10,548,591 B2
(45) Date of Patent: Feb. 4, 2020

(54) SURGICAL INSTRUMENTS

(71) Applicant: Roman Kelner, Northbrook, IL (US)

(72) Inventor: Roman Kelner, Northbrook, IL (US)

( * ) Notice: Subject to any disclaimer, the term of this patent is extended or adjusted under 35 U.S.C. 154(b) by 63 days.

(21) Appl. No.: 15/409,011

(22) Filed: Jan. 18, 2017

(65) Prior Publication Data

US 2018/0199936 A1 Jul. 19, 2018

(51) Int. Cl.
*A61B 17/06* (2006.01)
*A61B 17/062* (2006.01)

(52) U.S. Cl.
CPC .. *A61B 17/06004* (2013.01); *A61B 17/06166* (2013.01); *A61B 17/062* (2013.01); *A61B 17/06114* (2013.01); *A61B 2017/0609* (2013.01); *A61B 2017/06033* (2013.01); *A61B 2017/06038* (2013.01); *A61B 2017/06047* (2013.01); *A61B 2017/06057* (2013.01); *A61B 2017/06071* (2013.01)

(58) Field of Classification Search
CPC ........ A61B 17/06004; A61B 17/06166; A61B 17/06114; A61B 2017/06019; A61B 2017/06038; A61B 2017/06047; A61B 2017/06033
USPC ........................................................ 606/224
See application file for complete search history.

(56) References Cited

U.S. PATENT DOCUMENTS

| | | | |
|---|---|---|---|
| 2,516,710 A | 7/1950 | Mascolo | |
| 4,660,559 A * | 4/1987 | McGregor | A61B 17/06004 606/226 |
| 5,437,680 A * | 8/1995 | Yoon | A61B 17/0057 606/139 |
| 5,792,180 A | 8/1998 | Munoz | |
| 5,865,836 A * | 2/1999 | Miller | A61B 17/06 606/222 |
| 5,913,875 A | 6/1999 | Smith et al. | |
| 8,192,462 B2 | 6/2012 | Sulamanidze et al. | |
| 2007/0219586 A1* | 9/2007 | Mahadevan | A61B 17/06066 606/223 |
| 2009/0143819 A1* | 6/2009 | D'Agostino | A61L 17/12 606/228 |

(Continued)

FOREIGN PATENT DOCUMENTS

| | | | |
|---|---|---|---|
| DE | 19706086 A1 | 11/1997 | |
| EP | 0205811 A1 * | 12/1986 | ....... A61B 17/06004 |

(Continued)

*Primary Examiner* — Eric J Rosen
*Assistant Examiner* — Andrew P. Restaino
(74) *Attorney, Agent, or Firm* — Wood, Phillips, Katz, Clark & Mortimer (57) ABSTRACT

In one form, a surgical needle has a curved needle body having a first end and a second end and defines an interior region between the first and second ends. The interior region contains a center of curvature of the needle body. The first and second ends each terminate in a point. The needle body has an intermediate portion between the first and second ends, and defines an internal surface facing the interior region and an external surface facing away from the interior region. A recess is thrilled within the external surface of the needle body. In another form, the needle is provided in a sterilized package together with one or more elongate filaments each having a proximal end coupled to the needle body within the recess. A container holds the surgical needle and the filament.

2 Claims, 5 Drawing Sheets

(56) References Cited

U.S. PATENT DOCUMENTS

2011/0257663 A1* 10/2011 Unsworth .............. A01K 91/04
                                                     606/144
2012/0123471 A1   5/2012 Woodard, Jr. et al.
2012/0123472 A1*  5/2012 Culligan .......... A61B 17/06114
                                                     606/224
2018/0078255 A1*  3/2018 Dumanian ............. A61L 17/00

FOREIGN PATENT DOCUMENTS

EP       0205811 A1 * 12/1986  ....... A61B 17/06004
EP       0985382 A1 *  3/2000  ....... A61B 17/06066
EP       0985382 A1 *  3/2000  ....... A61B 17/06066
WO    2006011824 A1     2/2006

* cited by examiner

SURGICAL INSTRUMENTS

FIELD OF THE INVENTION

This disclosure relates to surgical instruments, and more particularly, to a surgical instrument for hand suturing organic anatomical structures.

BACKGROUND OF THE INVENTION

Surgical stitches have been used for more than three thousand years to close wounds or otherwise join organic anatomical structures. More than half of the time during any procedure or surgery devoted to achieve tissue bonding, by placement of surgical stitches. Singular, interrupted stitches are the simplest type to create tissue bounding. At the same time, singular stitches are just stationary adhesion points, and spacing in-between stitches are interrupted approximation "gaps" of the wound's edges. Re-epithelization or filling the gaps by the specialized tissue cell layers, forming anatomical tissue structures like epidermal, muscle, or fascia layers, starts from formation of different types of connective tissue, which becomes the future base of scar formation. Each hand-placed singular stitch is accompanied by multiple surgical ties, which create a surgical suture knots. After trimming of access of suture material above the knots, some amount of suture materials permanently left in the wound. With time, these stitching materials became rejected by the body, turn into a source of purulent inflammation, and "spit out" by the body through infected fistulas. Single, uninterrupted sutures may result in unwanted tissue adhesion or cosmetically inferior outcomes. Therefore, single surgical stitches are not the optimum technology for wound closure.

Continuous uninterrupted stitches provide the flexible, steady, and sealed bounding for wound's edges, with marginal amount of suture left. Some sutures are made from absorbable surgical materials and do not require removing after wound's healing. Non-absorbable surgical sutures used in continuous uninterrupted stitches provides the same benefits for healing, but the suture filaments are removed from the forming scar as a single unit, preventing inflammatory or rejection body responses.

The most-often used surgical needle is a disposable, semi-circular, so called swaged surgical needles. A typical swaged needle is described in U.S. Pat. No. 5,913,875, which is incorporated by reference herein in its entirety, wherein a suture material or filament is secured to a swaged end of the surgical needle while the other, operative end is pointed in a taper or cutting edge.

Complex stitching techniques require more skills and time from the operating team using swaged needles. Therefore, in many instances the stitching is simplified. Multiple surgical specialties utilize a multilayered closure for the wound, including a layer of absorbable stitches on a sub-dermal single interrupted layer, then a sub-dermal line of inverted singular absorbable stitches (subdermal layer), covered by a layer of dermal singular, interrupted non-absorbable stitches or metal staples, and a surgical adhesive (e.g., Dermabond) layer at the end.

Some have attempted to develop a double-pointed needle, such as those needles disclosed in European Patent Application No. 0985382 of Baek Seung Jun and U.S. Pat. No. 2,516,710 of Delfino P. Mascolo. However, the inventor has found that such needles are either prone to brittle failure at the connection point between the filament and the needle and/or assembly required by the surgical team prior to use, and/or were not disposable and could aid in the spread of blood borne diseases.

The present invention is directed toward overcoming one or more of the problems discussed above with the prior art circular, swaged needles and the double-pointed needles.

SUMMARY OF THE INVENTION

The present invention relates to an improved surgical instrument for hand suturing organic anatomical structures.

In one aspect of the present invention, the instrument has the form of needle having a curved needle body with a first end and a second end. The needle body defines an interior region between the first and second ends. The interior region contains a center of curvature of the needle body. Each of the first and second ends terminates in a point. The needle body has an intermediate portion between the first and second ends, and defines an internal surface facing the interior region and an external surface facing away from the interior region. A recess is formed within the external surface for receiving at least one filament.

In another aspect of the present invention, the surgical instrument further includes an elongate filament having a proximal end and a distal end. The proximal end is coupled to the needle body within said recess.

In yet another aspect of the present invention, the intermediate portion of the needle body is collapsed at the recess around the filament proximal end within the needle body.

According to another aspect of the present invention, the filament proximal end is coupled with the needle body by one of an adhesive and a weld.

In still another aspect of the present invention, the surgical instrument further includes a second elongate filament having a proximal end and a distal end. The proximal end of the second elongate filament is coupled to the needle body within the recess, preferably in a tandem fashion generally along a central axis of the needle body.

In one form of the invention, the first filament is absorbable within organic tissue, while the second filament is non-absorbable within organic tissue.

In another form of the present invention, the intermediate portion of the needle body has at least one substantially flat surface.

In still another form of the present invention, the intermediate portion of the needle body has a generally trapezoidal shape.

In yet another form of the present invention the first and second ends of the needle body have a generally circular cross-sectional shape.

According to another aspect of the present invention, the needle body has a semi-elliptical shape.

According to still another aspect of the present invention, the needle body defines a minor axis and a major axis. The major axis length is between about 2 and 2.5 times greater than the minor axis length.

In one aspect of the present invention, the recess is formed at a central location on the needle body.

In yet another aspect of the present invention, a sterilized package is provided. The package includes a surgical instrument in the form of a needle having a curved needle body with a first end and a second end. The needle body defines an interior region between the first and second ends. The interior region contains a center of curvature of the needle body. Each of the first and second ends terminates in a point. The needle body has an intermediate portion between the first and second ends, and defines an internal surface facing the interior region and an external surface facing away from the interior region. A recess is formed within the external surface for receiving at least one filament.

The package further includes at least one elongate filament having a proximal end coupled to the needle body within the recess. The filament has a distal end.

The package further includes a container holding the surgical instrument and the elongate filament.

In one aspect of the present invention, the sterilized package further includes a second elongate filament having a proximal end coupled to the needle body within the recess. The second elongate filament has a distal end. In one form, the first elongate filament is absorbable in organic tissue and the second elongate filament is non-absorbable in organic tissue.

Other objects, features, and advantages of the invention will become apparent from a review of the entire specification, including the appended claims and drawings.

BRIEF DESCRIPTION OF THE DRAWINGS

FIG. 1 is a top plan view, taken from above, of a first illustrated embodiment the present invention in the form of a package, and FIG. 1 shows a needle, a pair of filaments coupled thereto, and a container holding the needle and filaments—the needle, filaments, and container together defining the package;

FIG. 2 is a top plan view of a second illustrated embodiment the present invention in the form of a needle, and FIG. 2 shows the needle prior to being coupled with one or more filaments;

FIG. 2A is a perspective view of the second illustrated embodiment the present invention in the form of a needle, and FIG. 2 shows the needle after being coupled with a pair of filaments;

FIG. 3 is a detailed, cross-sectional view of the needle shown in FIG. 2 taken along plane 3-3 in FIG. 2;

FIG. 4 is a detailed, cross-sectional view of the needle of FIG. 2, and FIG. 4 shows the subsequent attachment of the needle with a filament;

FIG. 5 is a detailed, cross-sectional view of the needle of FIG. 2, and FIG. 5 shows the subsequent attachment of the needle with a pair of filaments in a tandem configuration generally along the central axis of the needle body;

FIG. 8 is a cross-sectional view of the needles of FIG. 7, and FIG. 8 shows each of the needles joined with a filament; and FIG. 9 is a top plan view, taken from above, of another illustrated embodiment the present invention in the form of a package, and FIG. 9 shows a pair of needles coupled by a filament, and a container holding the needles and filament—the needles, filament, and container together defining the package.

DETAILED DESCRIPTION OF THE PREFERRED EMBODIMENT

Figure 1:
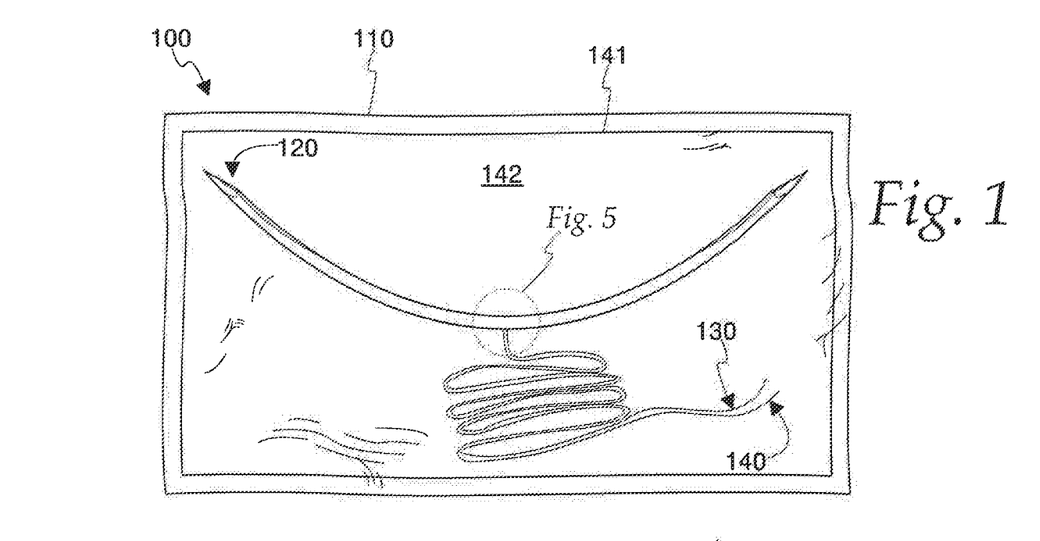

Referring now to FIG. 1, the numeral 100 indicates a first preferred embodiment of the present invention in the form of a sterile package. The package 100 has the basic components of a sealed container 110, an elliptical, double-pointed needle 120 connected together with a pair of sutures or threads 130 and 140. The container 110 may take a variety of forms, such as a breakable aluminum foil, blister pack, a sealed plastic, paper, or foil pouch, etc. Other types of containers may be used, such as a hard plastic case or box. Furthermore, the container may have the form of a cartridge for being assembled with a machine or larger medical device. The illustrated container 110 has a perimeter seal 141 defining a cavity 142 for retaining the needle 120 and the filaments 130/140. Preferably, the package 100 has the form of a sterilized, single-use product that may be safely opened by a physician or other medical professional, the needle 120 and filament 130/140 used to suture a wound, and then the needle 120, container 110, and remaining filament 130/140 of the package 100 may be disposed of.

Figure 2:
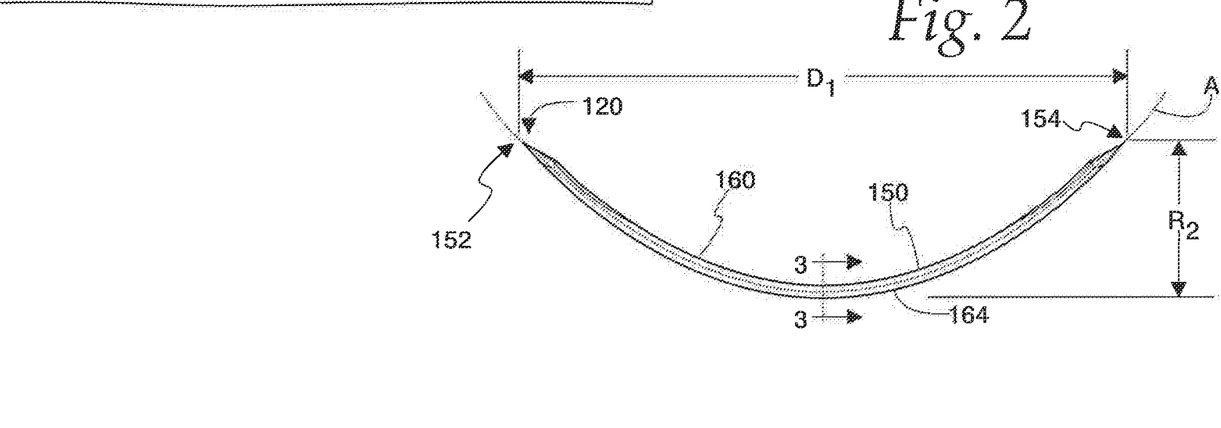

Referring now to FIG. 2, the needle 120 has a body 150 with a first operative, pointed end 152 and a second operative, pointed end 154. The needle body 150 is generally semi-elliptical when viewed from the side, having a major axis D1 and a minor axis (one half of which is designated as R2). The first and second pointed or piercing ends 152/154 are located generally at the major axis D1 of the ellipse defined by the needle body 150. The needle body 150 has a central axis "A" (FIG. 2) and a length along the central axis "A". The major axis D1 is preferably between about two and two and a half times as large as the minor axis (i.e., between about four and five times as large as R2). As described hereinafter, directions normal to the needle body central axis "A" are termed "radial" and directions along the axis "A", toward or away from the ends 152/154, are termed "axial". The needle body 150 has a surface defining a concave or interior side 160 and a convex or exterior side 164 of the needle 120. The needle body 150 has a generally circular cross-section (a plane taken normal to the axis "A") at the operative ends 152/154.

Figures 2A, 3, 4, 5:
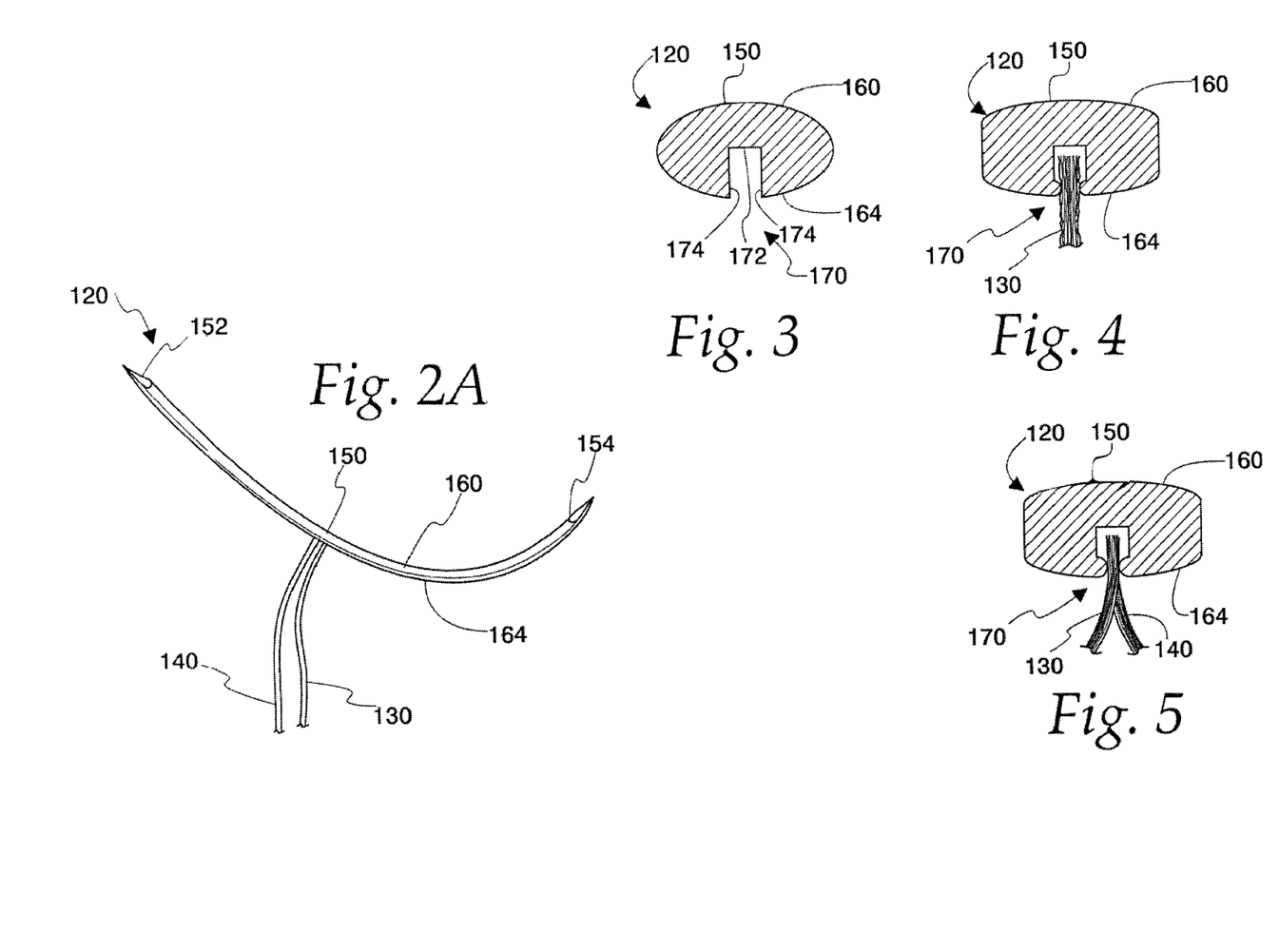

As can be seen in FIG. 3, the central region of the needle body 150 has a rounded, rectangular shape and has a channel or recess 170 formed therein. The recess 170 is formed on the exterior side 164 of the needle body 150 and functions to retain one or more filaments 130/140 that may be subsequently attached to the needle 120 (FIGS. 4 and 5). The recess 170 defines an interior end surface 172 and a pair of opposing interior side surfaces 174. With reference to FIG. 4, the manufacturer of the package 100 may join one end of the filament 130 with the needle 120 by compressing the metal needle body 150 to crimp or trap the end of the filament 130 within the recess 170. Other methods of joining the needle 120 with one or more filaments are anticipated, such as by applying an adhesive to join the filaments to the needle 120 within the recess 170. Alternatively, the material of the filament may be conducive to vibratory or heat welding. Furthermore, the filament may be provided with an intermediate body or end cap that may be force fit, glued, or welded within the recess 170. The filament 130 shown in FIG. 4 is a non-absorbable type (e.g., Nylon, Prolene, Novafil™, Polyester, silk, cotton, steel, etc.), but an absorbable filament may alternatively be used (e.g., collagen, surgical gut, (Catgut, Chromic Catgut), Monocryl, Vicryl, PDS, etc.) as a monofilament or braided suture material. It will be appreciated that the size of the recess 170 (e.g., depth and width) may be varied depending on the size and number of filaments that will be attached to the needle body 150, the shape of the needle body 150, and the method of joining the filaments together with the needle body 150.

With reference to FIG. 5, the manufacturer of the package 100 may alternatively join one end of multiple filaments (e.g., 130 and 140) together with the needle 120 by compressing the metal needle body 150 to crimp or trap one end of each of the filaments 130/140 within the recess 170. Other methods of joining the needle 120 with one or more filaments 130/140 are anticipated, as discussed in detail above. The filament 130 shown in FIG. 5 is a non-absorbable type (e.g., Nylon, Prolene, Novafil™, Polyester, silk, cotton, steel, etc.), while the filament 140 is an absorbable filament (e.g., collagen, surgical gut, (Catgut, Chromic Catgut), Monocryl, Vicryl, PDS, etc.). The filaments 130/140 may be monofilaments or braided. If a pair of filaments are used 130/140, then it would be preferable to configured them in a tandem manner along the central axis "A" of the needle body 150 to reduce the thickness or width of the needle body 150.

The needle body 150 is preferably formed from a surgical grade steel or steel alloy and may be formed in any gauge from 12-0 to 0-0. The needle body 150 may be alternatively be formed as a conventional cutting needle, reverse cutting, needle or tapered needle.

Figure 6:
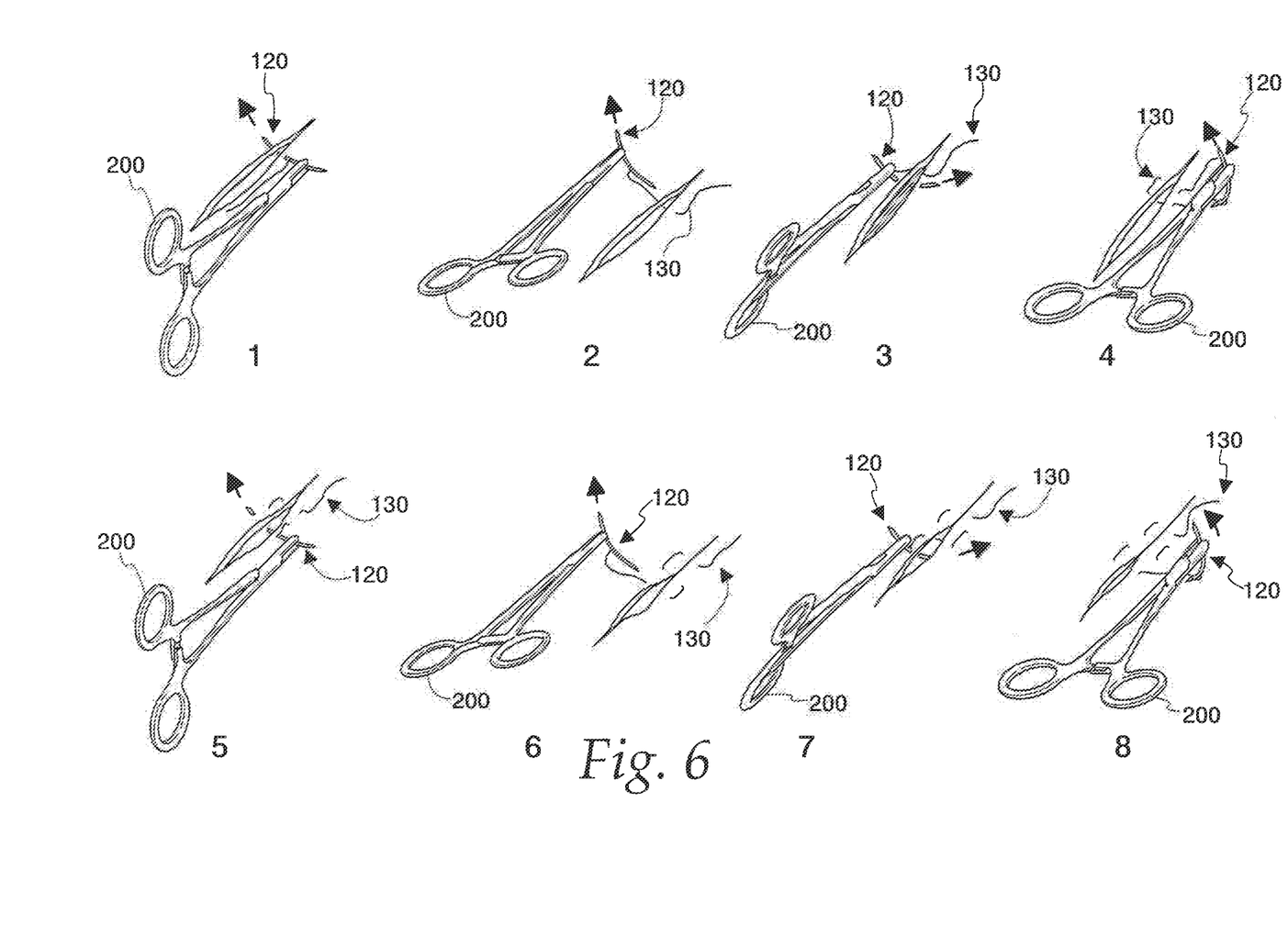
FIG. 6 illustrates a method of using the needle shown in FIG. 1.

One example of an operation of the needle 120, assembled together with a filament 130, will now be discussed with reference to FIG. 6. The central portion of the needle 120 is not circular in cross-section (as can be seen in FIG. 3), and may thus be easily grasped by a needle holder 200 or other gripping instrument. The double-pointed sterilized needle 120 and pre-attached filament 130 may have several advantages over the prior art semi-circular (⅜, ½, etc.) swaged needles. The elliptical shape of the needle 120 lends itself to being more easily grasped by the user while piercing tissue and passing the needle 120 through tissue. Furthermore, the double-pointed ends 152/154 of the needle 120 allow the needle 120 to be passed quickly and accurately through the tissue in a first direction and then returned in an opposite, second direction while eliminating excess steps of re-gripping and/or turning a swaged needle in the opposite, second direction through the tissue. The shape of the needle 120 with double-pointed ends 152/154 may eliminate the need for additional surgical instruments such as forceps. In a body cavity or space with limited access or visibility (e.g., such as during endoscopic or robotic surgery), the elliptical shape and double-pointed ends 152/154 of the needle 120 allow the user of the needle 120 to perform a simpler suturing motion (like a pendulum), as shown in FIG. 6, to reduce the duration of the surgery and improving the quality of healing. The inventor has found that the elliptical shape of the needle 120 described herein, along the minor axis, can allow for easier tissue penetration or tissue bite, particularly in the narrow portion of the surgical incision. In addition, the elliptical shape of the needle 120 described herein, along the major axis, can provide more mass penetration with each tissue bite. The partial, or semi-elliptical shape may further inhibit needle bending or disintegration in the "body" region through tough anatomical structures, like tendons, cartilage, bone, implanted plastic materials or combinations thereof.

While FIG. 6 shows the needle 120 used with only a single filament 130, it will be understood that a second filament 140 could be used simultaneously. If one of the two filaments 130/140 is a non-absorbable material, then the non-absorbable suture may be removed in a few days after surgery to avoid formation of stitch marks, while the absorbable filament may hold together the edges of the wound for a prolonged time period of months.

The inventor has further found that the design of the needle 120 allows for multiple filaments 130/140 to be assembled in-line within the needle body 150 without requiring an increase in the gauge or thickness of the needle, as would be the case for a swaged-type prior art needle.

Figure 7:
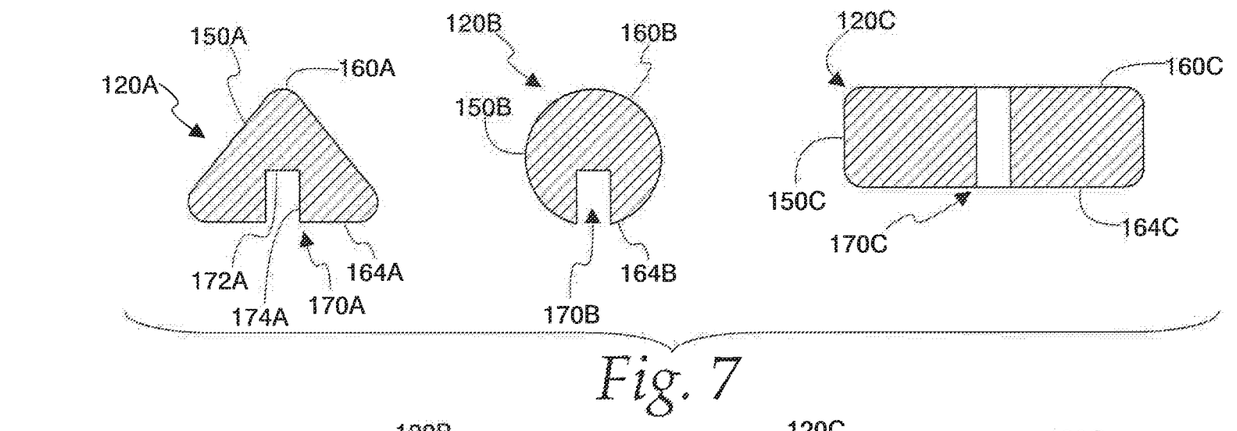
FIG. 7 is a cross-sectional view of several different embodiments of needles embodying the present invention, taken through the center of each needle.

FIG. 7 illustrates a number of alternate embodiments of a needle 120A, 120B, and 120C that are similar to the first illustrated embodiment of the needle 120. Like numerals are used herein throughout to denote like components between the first embodiment of the needle 100 and subsequent embodiments discussed, with the subsequent embodiment components denoted by the suffix "A", "B", "C", and so on. FIG. 7 shows a normal cross-section taken through the center region of the needles, similar to the cross-section of FIG. 2.

Figure 8:
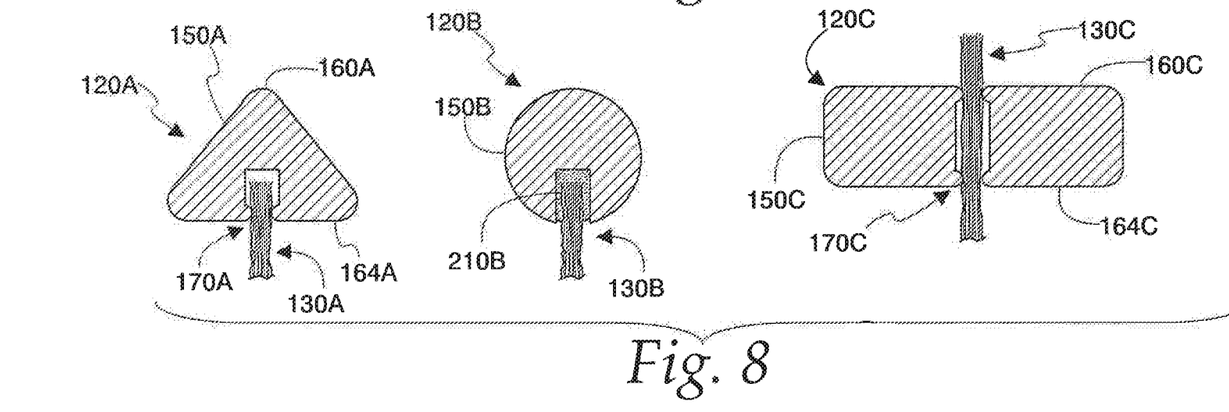

Needle 120A has an elliptical needle body 150A with a surface defining a concave or interior side 160A and a convex or exterior side 164A. The central portion or region of the needle body 150A has a channel or recess 170A formed therein. The recess 170A is formed on the exterior side 164A of the needle body 150A and also functions to retain one or more filaments that may be subsequently attached to the needle 120A (e.g., FIG. 8). The recess 170A defines an interior end surface 172A and a pair of opposing interior side surfaces 174A.

The second embodiment of the needle 120A differs from the first embodiment of the needle 120 in that the second embodiment of the needle 120E has a central portion or region having a generally trapezoidal shape with rounded corners. The second embodiment of the needle 120A otherwise functions identically as described above with respect to the first embodiment of the needle 120, and the needle 120A is similarly assembled with a filament 130A (FIG. 8) by way of compression of the metal needle body 150A to crimp or secure the filament 130A.

Needle 120B also has an elliptical needle body 150B with a surface defining a concave or interior side 160B and a convex or exterior side 164B. The central portion or region of the needle body 1501 has a channel or recess 170B formed on the exterior side 164B also functions to retain one or more filaments that may be subsequently attached to the needle 120B (e.g., FIG. 8).

The third embodiment of the needle 120B differs from the first embodiment of the needle 120 in a number of ways. First, the needle 120B has a central portion or region having a circular shape. The entire length of the needle body 150B has circular cross-sections when taken normal to the central body axis. The circular cross-sectional shape of the needle body 150B lends itself to being more easily manufactured than the first embodiment of the needle 120, however the lack of a flat side on the needle body 150B makes the needle 120B more difficult to grasp with a surgical tool such as a needle holder. In addition, the needle 120B is connected with a filament 130B (FIG. 8) by an intermediate adhesive or plug formed at one end of the filament 130B. The plug functions to provide a means of attaching the filament 130B to the needle body 150B other than crimping of the needle body 150B, such as by three fit of the plug into the needle body, heat or ultrasonic welding, adhesion, etc. The needle 1201 otherwise functions identically as described above with respect to the first embodiment of the needle 120.

Finally, needle 120C has an elliptical needle body 150C with a surface defining a concave or interior side 160C and a convex or exterior side 164C. The central portion or region of the needle body 150C has a through hole 170C formed between the exterior side 164C and the interior side 160C also functions to retain one or more filaments that may be subsequently attached to the needle 120C (e.g., FIG. 8).

The fourth embodiment of the needle 120C differs from the first embodiment of the needle 120 in that the needle 120C is connected with a filament 130C (FIG. 8) that extends through the hole 170C. The needle 120C is assembled with a filament 130C by way of compression of the metal needle body 130C to crimp or secure the filament 130C.

The needle 120C otherwise functions identically as described above with respect to the first embodiment of the needle 120.

Figure 9:
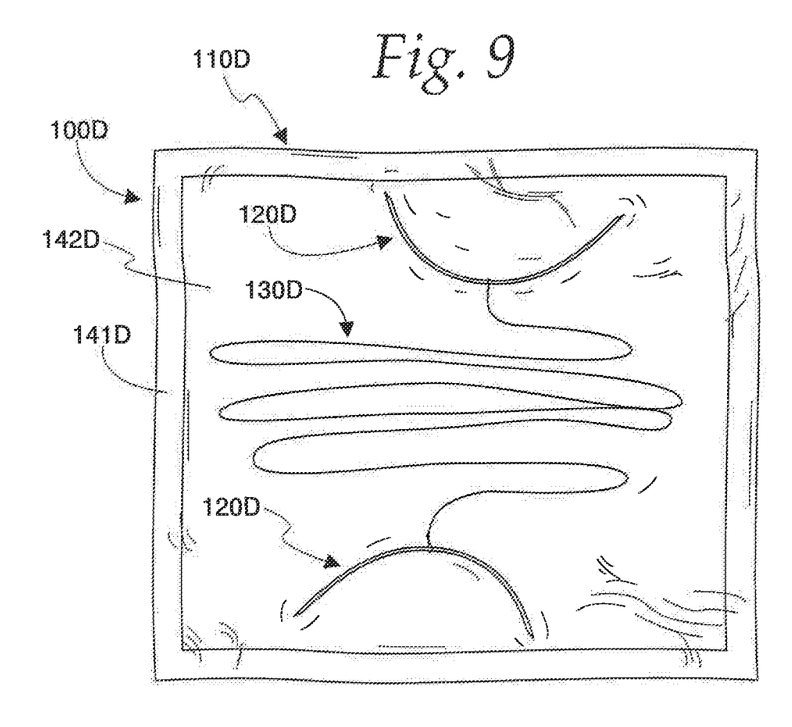

Referring now to FIG. 9, the numeral 100D indicates another embodiment of the present invention in the form of a sterile package. The package 100D has the basic components of a sealed container 110D, two elliptical, double-pointed needles 120D connected together with a suture or thread 130D. The container 110D may take a variety of forms, such as a breakable aluminum foil, blister pack, a sealed plastic, paper, or foil pouch, etc. Other types of containers may be used, such as a hard plastic case or box. Furthermore, the container 100D may have the form of a cartridge for being assembled with a machine or larger medical device. The illustrated container 110D has a perimeter seal 141D defining a cavity 142D for retaining the needles 120D and the filament 130D. Preferably, the package 100D has the form of a sterilized, single-use product that may be safely opened by a physician or other medical professional, the needles 120D and filament 130D used to suture a wound, and then the needles 120D, container 110D, and filament 130D of the package 100D may be disposed of.

The provision of a pair of needles 120D connected by a filament 130D forms a double-armed surgical suture that provides the advantage of the ability to start surgical suturing from a central part of an incision, whereby the suture may proceed in two directions. Each individual needle 120D may be formed as described above with respect to any of the other embodiments. It is further anticipated that multiple filaments may be used with the needles 120D.

The foregoing disclosure of specific embodiments is intended to be illustrative of the broad concepts comprehended by the invention. Various modifications and alterations to this invention will become apparent to those skilled in the art without departing from the scope and spirit of this invention. The illustrative embodiments are provided as an example only and are not intended to limit the scope of the present invention.

The invention claimed is:

1. A surgical instrument comprising:
a curved needle body having a first end and a second end and defining a convex exterior side and a concave interior side, said concave interior side facing a center of curvature of said needle body, said first and second ends each terminating in a point, said needle body having an intermediate portion between said first and second ends, and a recess formed within said exterior side at said intermediate portion for receiving at least one filament, said needle body has a central axis extending through a geometric center of said needle body from said first end and said second end, a first elongate filament having a proximal end and a distal end, said proximal end being coupled to said needle body within said recess, and a second elongate filament that is separate from said first elongate filament, said second elongate filament having a proximal end and a distal end, said proximal end coupled to said needle body within said recess, and wherein said proximal end of said first filament and said proximal end of said second filament are coupled to said needle body within said recess in a tandem configuration, one in front of the other, along said central axis when viewed in a cross-sectional plane taken normal to said central axis at said recess.

2. The surgical instrument as recited in claim 1 wherein said first filament is absorbable within organic tissue, and said second filament is nonabsorbable within organic tissue.

* * * * *